United States Patent [19]

Goldovsky et al.

[11] Patent Number: 4,963,023
[45] Date of Patent: Oct. 16, 1990

[54] CORRELATIONAL GAS ANALYZER

[76] Inventors: Viktor L. Goldovsky, ulitsa Shopena, 18, kv. 6, Uzhgorod; Viktor I. Stetsovich, ulitsa Donskaya, 33, Uzhgorod; Andrei J. Zayats, ulitsa Gagarina, 27a, all of, Uzhgorod, all of U.S.S.R.

[21] Appl. No.: 339,497

[22] Filed: Apr. 17, 1989

[51] Int. Cl.$^5$ .................. G01J 3/06; G01J 3/32; G01N 21/35
[52] U.S. Cl. .................. 356/308; 250/339; 356/328
[58] Field of Search .............. 356/308, 310, 326, 328, 356/334; 250/339

[56] References Cited

U.S. PATENT DOCUMENTS

| 2,849,618 | 8/1958 | Smith | 250/339 |
| 4,575,243 | 3/1986 | Witte | 356/308 X |

OTHER PUBLICATIONS

Prikladnaya infrakrasnaya spektroskopiya, Ed. D. Kendall, Moscow, MIR Publishers 1970.
R. Haulet, C. Vavasseur, "Teledetection des pollutants gaseoux de l'atmospher", Bull. inform. sci, et techn, 1978, 230/231, p. 59.

*Primary Examiner*—Vincent P. McGraw
*Attorney, Agent, or Firm*—Lilling and Lilling

[57] ABSTRACT

A correlational gas analyzer, comprising a light source with the light beam passed through the gas under study with a quasiperiodic pattern of the spectral band, and an optical system with sequentially positioned along the light beam condensor, input slit iris, beam dispering element and rotatably mounted output slit iris configured as a disc with a slit shaped as an Archimedes spiral. The Archimedes spiral center is coincident with the disc center and its pitch is approximately equal to the scan length of the specified spectral band of the gas under study. The output slit iris scans the specified spectral band of the gas under study across a photoreceiver, the outputs whereof drive the inputs of a first and second electric signal amplifier, with the outputs thereof connected to connected in series corrector unit and recorder. The first amplifier is a tuned amplifier with resonant frequency defined by the speed of disc rotation and by the number of maxima or minima in the specified spectral band of the gas under study.

3 Claims, 2 Drawing Sheets

CORRELATIONAL GAS ANALYZER

FIELD OF THE INVENTION

This invention relates to optical instrumentation and more specifically to correlational gas analyzers.

This invention can be used in chemical industry to analyse compositions of gas mixtures, in microelectronics to monitor the gas composition of air in the work zone, in metallurgy and other industries. This invention can also be successfully employed in environment control to monitor pollution by exhaust gases, e.g. $SO_2$, $NO_2$, NO, $NH_3$, etc.

BACKGROUND OF THE INVENTION

Currently most high-selectivity gas analyzers are based on correlational spectroscopy, wherein gas concentrations are determined from characteristic features of the spectra of gases under analysis, such, e.g., as the quasiperiodic structures of absorption or transmission spectra. These gas analyzers should be capable to perform multicomponent analysis of the gas under study without essentially complicating their design and also feature simplicity of conversion to measurement of the content of another gas in the mixture.

Known in the art is a correlational gas analyzer ("Prikladnaya infrakrasnaya spektroskopiya", Ed. D. Kendall, Moscow, MIR Publishers, 1970) comprising a light source and positioned in sequence along the beam path interference filter to select the specified spectral band of the gas under analysis, a modulator, two cells with one cell thereof filled by the gas under analysis and the second cell thereof filled with a gas that does not absorb radiation in the selected spectral band, a photoreceiver, and a recorder.

After passing through the cell filled with the gas under analysis the light beam does not contain spectral components corresponding to absorption lines, while at the output of the other cell it contains all spectral components of the selected for gas analysis spectral band. The photoreceiver generates a signal proportional to light attenuation due to absorption in the gas under analysis and this signal allows detection and assessment of concentration of the gas under analysis positioned in the beam path between the light source and photoreceiver.

The known in the art gas analyzer features poor accuracy and low reproducibility of measurement results due to absorption of the gas under analysis and its leakage out of the cell. In cases of corrosive gases, such as $H_2S$ and $SO_2$, and unstable gases, such as $NO_2$, using this gas analyzer is hampered by the necessity to maintain constant temperature and humidity.

Also known in the art is a correlational gas analyzer (R. Haulet, C. Vavasseur "Teledetection des pollutants gaseoux de l'atmosphere" Bull. inform. sci. et techn., 1978, 230/231, p. 59) comprising a light source, the beam whereof passes through the gas under study with a quasiperiodic spectrum pattern in the specified spectral band, and through an optical system comprising sequentially positioned along the beam path condensor, input slit iris, dispersing element, and output slit iris mounted rotatably and configured as a disc with a slit to scan the specified spectral band arriving at the photoreceiver, with the output thereof electrically connected to the input of a recorder via an electric signal amplifier.

This known in the art correlational gas analyzer uses a concave grating as the dispersing element, while the slits in the disc are configured as arcs and positioned so as to coincide with maxima and minima in the absorption spectrum of the gas under study in the focal plane of the concave grating.

The light beam passed through the gas under analysis is decomposed into a spectrum by the concave grating and then passed via the slits of the rotating disc. Thus the spectral band of the gas under study is scanned by the photoreceiver, the modulation depth of the light beam being proportional to difference in intensities of corresponding transmission and absorption areas in the spectral band of the gas under study and depends, therefore, on the content of the gas under study in the volume.

The optical system of this known in the art gas analyzer is complicated and therefore hard to manufacture, as is the alignment of the disc, the slits whereof have to be precisely aligned to the maxima and minima of the absorption spectrum of the gas under study, this alignment being critical to the measurement accuracy and reproducibility. Conversion to measurements of another gas component requires replacement of the disc with another, featuring corresponding slits, and its alignment in the optical system.

SUMMARY OF THE INVENTION

The objective of this invention is to provide a correlational gas analyzer allowing analysis of multicomponent gas mixtures without replacements of the disc in the optical system.

This is achieved by that in a correlational gas analyzer comprising a light source, the radiation beam whereof passes through the gas under study with a quasiperiodic pattern of the specified spectral band, and an optical system comprising sequentially positioned along the beam path condensor, input slit iris, dispersing element, and rotatably mounted output slit iris configured as a disc with a slit to scan the specified spectral band at the photoreceiver, the output thereof electrically connected to the input of a recorder via an amplifier of electric signals, according to the invention the slit in the output slit iris is configured as an Archimedes spiral with centre coinciding with the disc centre and pitch approximately equalling the scan length of the specified spectral band of quasiperiodic pattern in the scan plane, further provided is an additional electric signal amplifier with the input thereof connected to the photoreceiver output, and a corrector unit with inputs thereof connected to the outputs of the master and additional electric signal amplifiers and with the output thereof connected to the recorder input, wherein the master electric signal amplifier is a tuned amplifier with the resonant frequency thereof defined by the disc rotation speed and the number of maxima and minima in the specified spectral band with a quasiperiodic pattern of the gas under study.

It is advantageous to define the resonant frequency of the master electric signal amplifier from the relation $f_1 = (\Delta\lambda\delta\lambda)N$, where $\Delta\lambda$ is the specified spectral band of the gas under study featuring a quasiperiodic pattern, $\delta\lambda$ is the period of pattern of specified spectral band of the gas under study, and N is the disc rotation speed.

It is also advantageous that the additional electric signal amplifier be a tuned amplifier with the resonant frequency thereof differing from that of the master electric signal amplifier and defined by the speed of disc rotation.

The correlational gas analyzer of the invention allows studies of the gas components of multicomponent gas mixtures without disc replacement in the optical system, thus essentially reducing the measurement error due to inaccuracy of disc alignment in the optical system.

Fabricating a slit in the disc, configured as an Archimedes spiral presents no difficulties and is easily adaptable to streamline production, being programmable with known formula for numerically controlled lathes.

Two tuned amplifiers and a corrector unit in the correlational gas analyzer circuitry improve immunity to various interference and thus significantly reduce the measurement error.

BRIEF DESCRIPTION OF ACCOMPANYING DRAWINGS

These objectives of the invention will become apparent from the following description of the invention and accompanying drawings, wherein:

FIG. 1 schematically shows the correlational gas analyzer of the invention, with a sectional view of the optical system;

FIG. 2 shows the disc with a slit configured as Archimedes spiral and the spectral of $NH_3$ and $SO_2$ aligned to the slit's position.

DETAILED DESCRIPTION OF THE INVENTION

Figure 1:
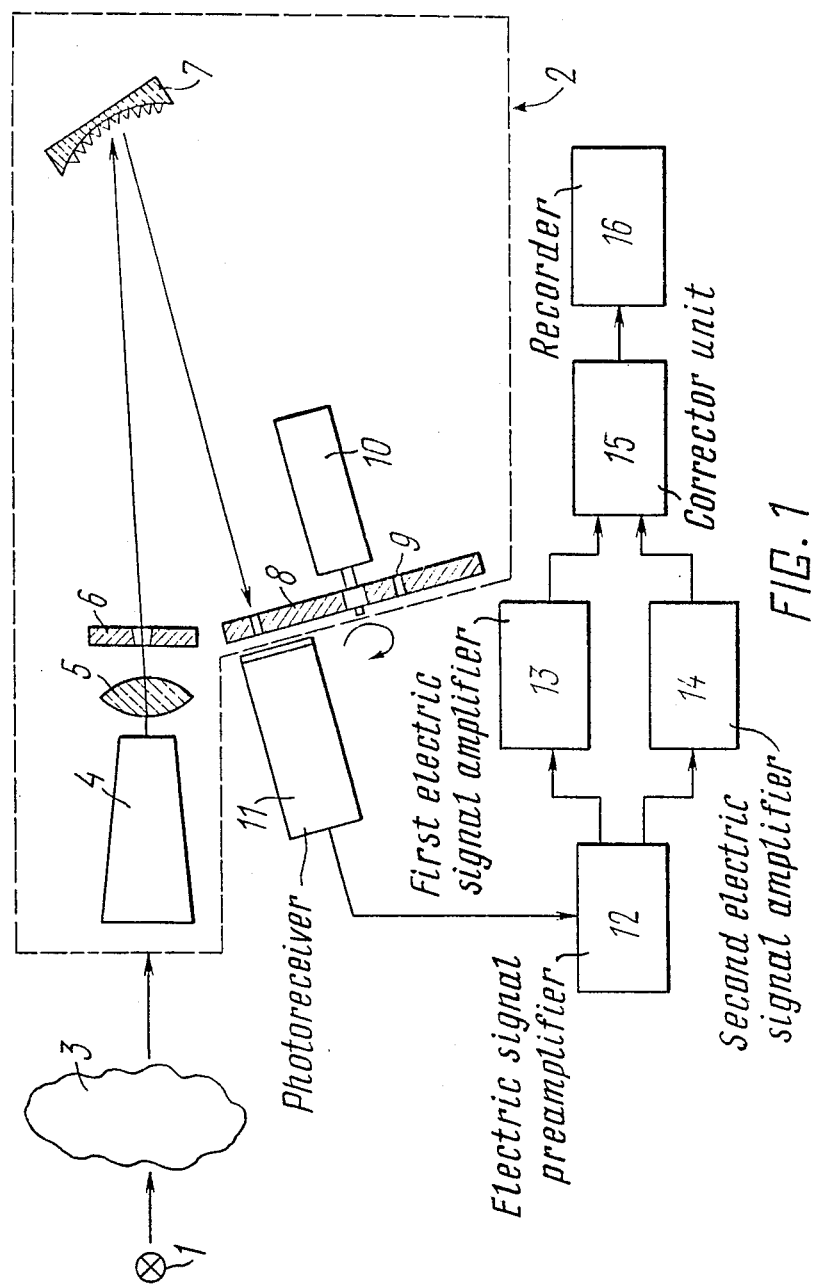

The correlational gas analyzer comprises light source 1 (FIG. 1), which may be an artificial source or natural source (Sun or Moon) of light, and optical system 2. The gas under study 3 is positioned between light source 1 and optical system 2; gas 3 features a quasiperiodic spectrum pattern in the specified spectral band and may be in the atmosphere or contained in a special cell.

In the embodiment being described, optical system 2 comprises sequentially positioned along the beam path blind 4 to exlude scattered light, condensor 5 in the form of a biconvex lens to focus the light beam onto input slit iris 6, dispersing element 7 in the form of a concave grating (in the following—grating 7) and rotatably mounted output slit iris 8 with slit 9 configured as an Archimedes spiral and rotated by motor 10. Photoreceiver 11 is positioned in the beam path downstream relative to output slit iris 8 and drives the input of electric signal preamplifier 12, with the output thereof connected to the inputs of electric signal amplifiers 13, 14. Electric signal amplifier 13 is tuned and its resonant frequency $f_1$ is defined by the relation $f_1 = (\Delta\lambda/\delta\lambda)N$, where $\Delta\lambda$ is the specified spectral band of gas under study with a quasiperiodical spectrum pattern, $\delta\lambda$ is the period of this pattern of the spectrum of gas 3, and N is the speed of disc 8 rotation.

Electric signal amplifier 14 is tuned to resonance frequency $f_2$ defined by disc 8 rotation speed and serves to compensate instabilities in tuned amplifier 13 output signal due to variations of light beam intensity.

In another embodiment a DC amplifier may be employed as amplifier 14, with outputs of amplifiers 13, 14 connected to the inputs of corrector unit 15, the output thereof connected to recorder 16 calibrated in units of gas under study concentration.

Figure 2:
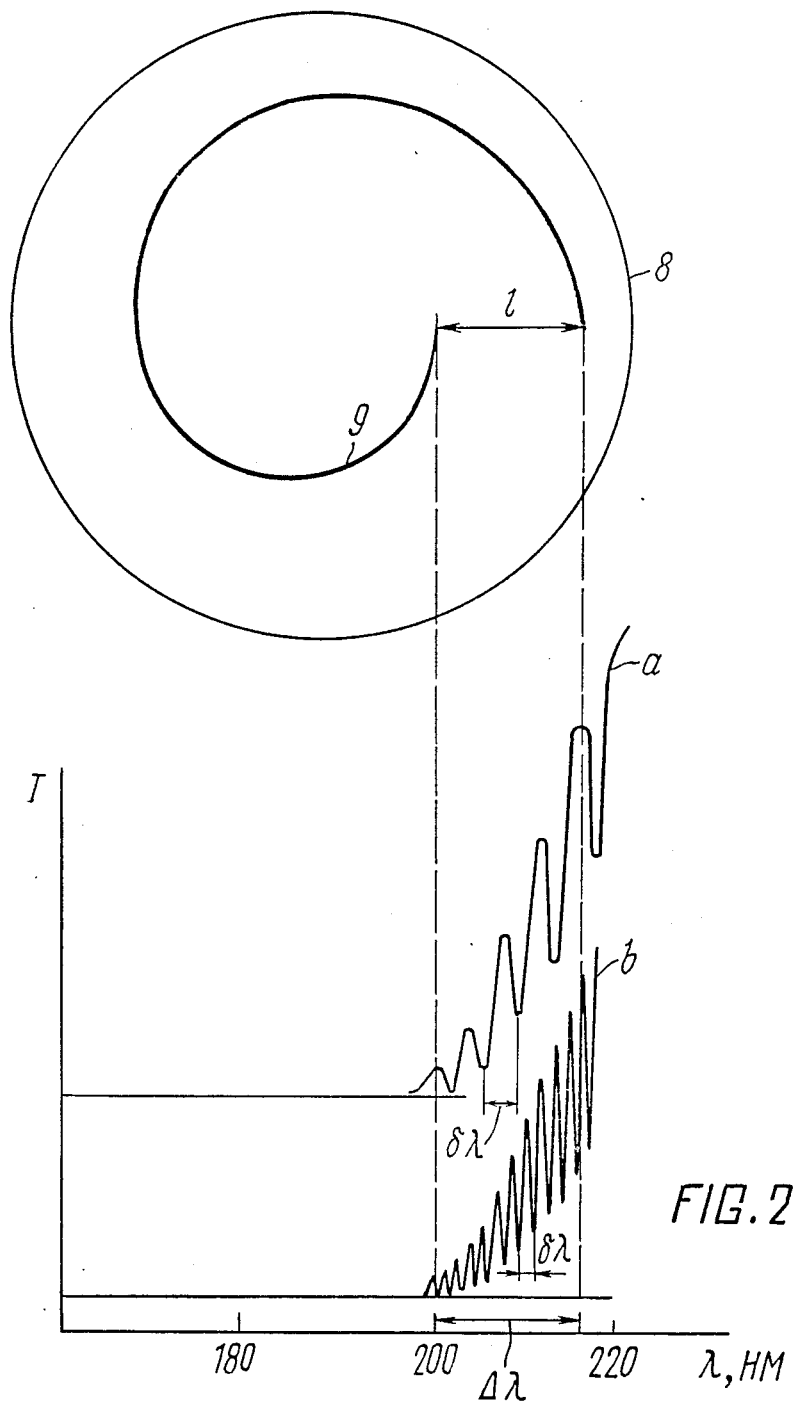

FIG. 2 shows disc 8 with slit 9 configured as Archimedes spiral with centre aligned to disc 8 centre and pitch 1 approximately equal to the scan length of the specified spectral band $\Delta\lambda$ of gas 3 under study with a quasiperiodic spectrum pattern, in the focal plane of concave grating 7 (FIG. 1) serving as the scan plane in the embodiment being described. For presentation explicitness the specified transmission band for $NH_3$ and $SO_2$ (FIG. 2, curves a, b) are aligned in the drawing with disc 8 slit 9 positioning.

The wavelength, $\lambda$, of the spectrum of gases 3 under study is plotted along the abscissa axis in nanometers, with the transmissivity, T, plotted along the ordinate axis in relative units and the spectra for $NH_3$ and $SO_2$ displaced one relative to another along the ordinate axis for convenience of presentation.

The correlational gas analyzer according to the invention functions as follows.

Light radiation from light source 1 (FIG. 1) passes through gas 3 under study and its spectrum acquires a typical quasiperiodic pattern in the specified spectral band $\Delta\lambda$ in accordance to FIG. 2. The light beam then arrives via blind 4 to exclude scattered light and focusing condensor 5 at input slit iris 6. After passing input slit iris 6 the light beam arrives at concave grating 7 which disperses the light beam in the specified spectral band (FIG. 2) of the gas under study and focuses it in its focal plane. Rotating disc 8 with slit 9 configured as Archimedes spiral is positioned in said focal plane and provides continuous time scanning of specified spectral band $\Delta\lambda$ (FIG. 2) of gas 3 under study at photoreceiver 11, wherein the scanned light radiation is converted into an electric signal to drive preamplifier 12. The amplified signal is applied to the inputs of electric signal amplifiers 13, 14, the first thereof separates and amplifies signals of $f_1$ frequency and suppresses signals of all other frequencies. In case of transmission spectra shown in FIG. 2 for $NH_3$ (curve a) and $SO_2$ (curve b) the specified spectral band, $\Delta\lambda$, with a quasiperiodic pattern constitutes 200 nm to 215.5 nm and the pattern period, $\delta\lambda$, is 3.8 nm and 1.6 nm, respectively. At a disc 8 rotation speed N=60 revolutions per second, the resonant frequency, $f_1$, is 140 Hz for $NH_3$ and 600 Hz for $SO_2$.

Thus, for $NH_3$ concentration analysis amplifier 13 is tuned to a frequency of 240 Hz, or to 600 Hz for $So_2$ concentration analysis, with the amplitude of the its output signal corresponding to the concentration of the gas under study. In case of a tuned amplifier 14, its output signal is independent of the spectral characteristics of the gas under study and is at a frequency $f_2$, which characterizes the scanning process and ensures suppression of all other frequencies arrising from the effects of various interference. The output signals of amplifiers 13, 14 are then applied to the inputs of corrector unit 15, where the amplitude of the signal of $f_1$ is reduced to that of the $f_2$ signal. Thus, variations in signal $f_1$ amplitude caused by variations of the light beam intensity due to non-selective absorption in the beam path and to changes in light source 1 parameters are cancelled out, resulting in an improved accuracy of measurements. The reduced signal from corrector unit 15 output arrives at the input of recorder 16 for display of the concentration of gas 3 under study in digital or analogue format.

In cases when optical system 2 and light source 1 are housed in a common casing and thus the entire optical path is protected against extraneous illumination, it is preferrable to use a DC amplifier as amplifier 14 and reduce the amplitude of signal $f_1$ in corrector unit 15 to the DC component, with signal recording as described above.

To convert to measurements of another component concentration in the gas mixture it is sufficient to retune tuned amplifier 13 to a resonant frequency $f_1$ corresponding to the spectral characteristics $\Delta\lambda$, $\delta\lambda$ of this new component. No replacements of disc 8 and realignments of optical system 2 are necessary, this essentially improving the accuracy of measurements.

Thus, the correlational gas analyzer according to the invention features low production cost and simplicity of optical system alignment and use.

What is claimed is:

1. A correlational gas analyzer, comprising:
    a light source with the light beam thereof passed through the gas under study featuring a quasiperiodic pattern in the specified spectral band described the number of maxima and minima and pattern pitch;
    an optical system positioned downstream of the light beam path after the gas under study with a quasiperiodic pattern of the specified spectral band and comprising:
    a condensor;
    an input slit iris;
    a dispersing element;
    an output slit iris rotatably mounted and rotated at a specified speed, this iris configured as a disk with a slit to scan the specified spectral band of the gas under study and configured as an Archimedes spiral with spiral centre coincident with disc centre and spiral pitch approximately equal to the scan length of the specified spectral band of the gas under study with the focal plane of the dispersing elements serves as the scan plane;
    a photoreceiver to receive the light beam after passage via said output slit iris;
    first electric signal amplifier with input connected to the output of said photoreceiver, designed as a tuned amplifier and tuned to a frequency defined by said disc rotation speed and by the number of maxima and minima in the specified spectral band of the gas under study with a quasiperiodic spectrum pattern;
    a second electric signal amplifier with input connected to the output of said photoreceiver;
    a corrector unit with inputs connected to the outputs of said first and said second electric signal amplifier;
    a recorder with input connected to the output of said corrector unit.

2. The correlational gas analyzer as substantially set forth in claim 1, wherein the resonant frequency $f_1$ of said first amplifier is defined by the relation $f_1 = (\Delta\lambda/\delta\lambda)/N$, where $\delta\lambda$ is the specified spectral band of the gas under study with a quasiperiodic spectrum pattern, $\delta\lambda$ is pattern pitch of the spectral band of the gas under study and N is the disc rotation speed.

3. The correlational gas analyzer as substantially set forth in claim 2, wherein said second electric signal amplifier is a tuned amplifier with resonant frequency defined by the disc rotation speed.

* * * * *